US007455691B2

(12) United States Patent
Feingold et al.

(10) Patent No.: US 7,455,691 B2
(45) Date of Patent: Nov. 25, 2008

(54) INTRAOCULAR AND INTRACORNEAL REFRACTIVE LENSES

(75) Inventors: Vladimir Feingold, Laguna Hills, CA (US); Alexei Kosmynine, Aliso Viejo, CA (US)

(73) Assignee: Biovision, AG (CH)

(*) Notice: Subject to any disclaimer, the term of this patent is extended or adjusted under 35 U.S.C. 154(b) by 675 days.

(21) Appl. No.: 10/980,717

(22) Filed: Nov. 3, 2004

(65) Prior Publication Data

US 2006/0095127 A1 May 4, 2006

(51) Int. Cl.
*A61F 2/16* (2006.01)

(52) U.S. Cl. .................................................... 623/6.49

(58) Field of Classification Search ......... 623/6.17–6.5, 623/6.6, 6.62

See application file for complete search history.

(56) References Cited

U.S. PATENT DOCUMENTS 4,573,998 A 3/1986 Mazzocco
4,702,244 A 10/1987 Mazzocco
5,192,319 A 3/1993 Worst
5,217,491 A 6/1993 Vanderbilt
5,336,261 A 8/1994 Barrett et al.
5,609,630 A * 3/1997 Crozafon ................... 623/6.43
6,106,553 A 8/2000 Feingold
6,425,917 B1 * 7/2002 Blake ......................... 623/6.42
6,506,212 B2 * 1/2003 Zhou et al. ................. 623/6.38
6,537,316 B1 3/2003 Chambers
6,599,305 B1 7/2003 Feingold
6,629,979 B1 10/2003 Feingold et al.
6,666,887 B1 12/2003 Callahan et al.
6,712,848 B1 3/2004 Wolf et al.
6,755,859 B2 6/2004 Hoffmann et al.
2002/0103537 A1 8/2002 Willis et al.
2003/0033013 A1 * 2/2003 Callahan et al. ............ 623/6.21
2004/0068317 A1 4/2004 Knight
2004/0085511 A1 5/2004 Uno et al.
2005/0021140 A1 * 1/2005 Liao .......................... 623/6.37

* cited by examiner

*Primary Examiner*—Suzette J Gherbi
(74) *Attorney, Agent, or Firm*—Lawrence S. Cohen

(57) ABSTRACT

An intraocular and intracorneal lens includes an optical portion and a corrugated haptic portion. Corrugations of the haptic portion may be linear or arcuate, and such corrugations may be present on both anterior and posterior surfaces of the haptic portion. The intraocular lens may be deformed before or during insertion in an eye of a patient, and may be positioned in the posterior chamber of the eye such that the optical portion is spaced anteriorly from the crystalline lens of the eye. In alternative embodiments, an intraocular or intracorneal lens of the invention may be inserted in the anterior chamber, or within the cornea, of an eye of a patient. An alternative intraocular lens includes an optical portion having a peripheral optic zone and an inner non-optic zone. Methods for correcting visual deficiencies of a patient, by insertion of an intraocular or intracorneal lens of the invention in an eye of the patient, are also disclosed.

32 Claims, 12 Drawing Sheets

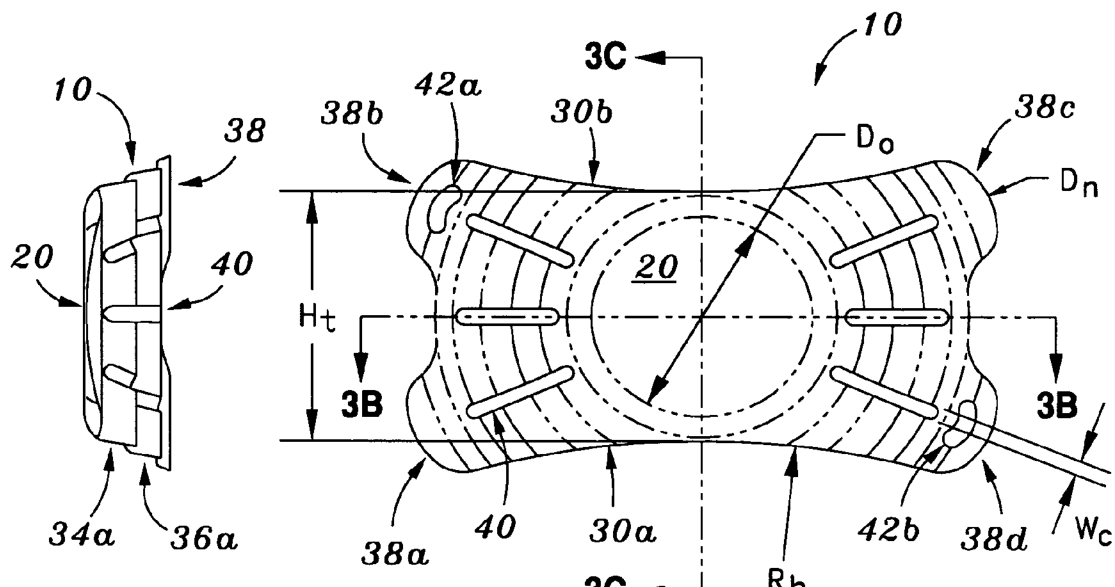
FIG. 3C
FIG. 3A
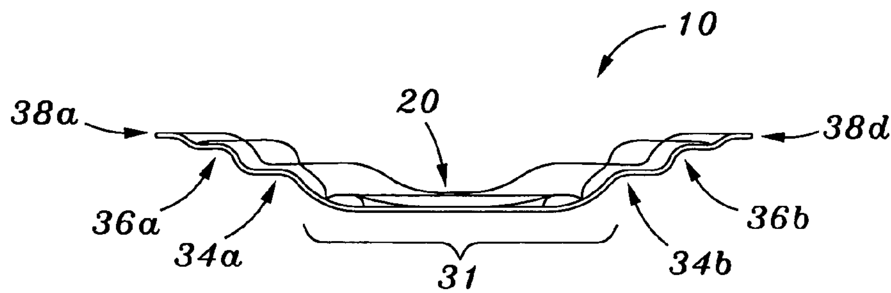
FIG. 3B
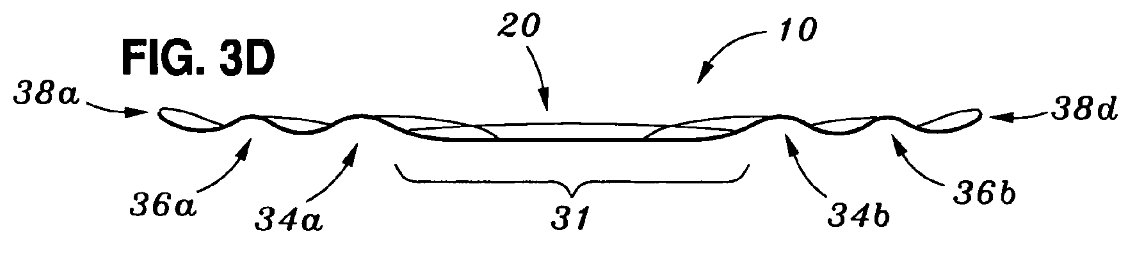
FIG. 3D
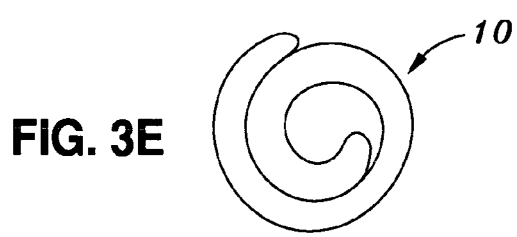
FIG. 3E

INTRAOCULAR AND INTRACORNEAL REFRACTIVE LENSES

BACKGROUND OF THE INVENTION

The present invention generally relates to intraocular and intracorneal refractive lenses, and to methods for correcting vision by insertion of an intraocular or intracorneal refractive lens in an eye of a patient.

Intraocular or intracorneal refractive lenses provide a viable alternative to spectacles and extra-ocular contact lenses for correcting deficiencies in visual acuity. Intraocular lenses (IOLs) of the prior art typically comprise an optical portion for refraction and a haptic portion for supporting the IOL in the anterior or posterior chamber of the eye. All or part of an IOL may be constructed from a deformable or flexible material. A deformable IOL has the advantage that it can be inserted in the eye via a smaller incision than an incision required to insert a non-deformable or rigid IOL of comparable dimensions. Larger incisions in the eye have many disadvantages, including longer patient recovery times, and increased risk of infection. However, the flexible nature of deformable IOLs typically present problems both in maneuvering the IOL during an insertion procedure, and in retaining the IOL in the correct position within the eye. To prevent the risk of damage or necrosis of ocular tissue following contact with, or penetration by, a portion of an IOL, rigid and/or pointed structures should be avoided.

Nevertheless, in an attempt to anchor the IOL in place within the eye, prior art IOLs have used clasps, pointed tips, and the like which penetrate iris tissue. For example, U.S. Pat. No. 6,755,859 B2 to Hoffmann et al. discloses an intraocular lens having an optical portion and two or more haptic elements for supporting the optic portion in the eye via a tissue clasp on each haptic element. US Patent Application Publication No. US 2002/0103537 A1 (Willis et al.) discloses an intraocular lens having an optic and a haptic, wherein the distal end of the haptic includes a pointed tip constructed and arranged to penetrate the iris. In a second embodiment of Willis et al., the intraocular lens is attached to the iris by a staple.

US Patent Application Publication No. US 2004/0085511 A1 (Uno et al.) discloses an intraocular lens having at least one pore near the center of the optical part of the lens, and a plurality of grooves in the back surface of the lens in a region that will make contact with the crystalline lens. The grooves allow fluid to flow towards the pores, and the pores allow fluid to flow through the lens. The intraocular lens of Uno et al. may also have circumferentially spaced protrusions, arranged in the boundary between the optical part and the support part of the lens, in an attempt to separate the optical part of the IOL from the crystalline lens. The diameter of the pores is restricted by potential deterioration in optical characteristics of the optical portion, e.g., reflection of light incident on the periphery of the pores. The location of the protrusions is limited by their potential to interfere with or restrict deformability of the lens for insertion in the eye.

U.S. Pat. No. 6,106,553 to Feingold discloses an intraocular lens having a shape that is predetermined with respect to a shape of the crystalline lens to form a spacing between at least part of the IOL and the crystalline lens. For example, the radius of arc of the posterior surface of an optic portion of the IOL may be smaller than the radius of arc of the posterior surface of a body portion of the IOL, so that the optic portion has a vaulted relationship to the anterior surface of the crystalline lens in the location of the pupil. In this relationship (e.g., FIG. 28 of the '553 patent), the body portion of the IOL is in contact with the crystalline lens at a position radially outward from the pupil. The IOL may have a circular groove that allows circulation of fluid in the eye (FIGS. 20 and 21 of the '553 patent).

As can be seen, there is a need for an intraocular lens which may be positioned in the eye, and held at a desired intraocular location, without penetrating or damaging the iris or other ocular tissue. There is a further need for an intraocular lens which allows the passage of aqueous humor therethrough without compromising the optical characteristics or performance of the IOL. There is a still further need for an intraocular lens which may be positioned in the posterior chamber of the eye such that the IOL does not contact the crystalline lens, and wherein the IOL is readily deformable for insertion in the eye.

SUMMARY OF THE INVENTION

In one aspect of the present invention, there is provided an intraocular lens which comprises an optical portion; and a haptic portion surrounding said optical portion, wherein the haptic portion is corrugated.

In another aspect of the present invention, an intraocular lens comprises an inner domed portion; and an outer portion having a plurality of tabs disposed peripherally on the outer portion, wherein the domed portion is spaced axially from the plurality of tabs.

In still another aspect of the present invention, an intraocular lens comprises a central optical portion; and an outer haptic portion, wherein the haptic portion includes an annular portion disposed adjacent to, and radially outward from, the optical portion; a pair of inner arcuate corrugations disposed adjacent to, and radially outward from, the annular portion, the pair of inner arcuate corrugations disposed on opposite sides of the optical portion; and a pair of outer arcuate corrugations disposed adjacent to, and radially outward from, the pair of inner arcuate corrugations.

In yet another aspect of the present invention, there is provided an intraocular lens comprising an optical portion including a peripheral optic zone, and an inner non-optic zone surrounded by the peripheral optic zone, wherein the peripheral optic zone has optical power, and the inner non-optic zone has no optical power.

In a further aspect of the present invention, there is provided a haptic for an intraocular lens, the intraocular lens including an optical portion, and the haptic comprising an annular portion encircling the optical portion; and at least one arcuate corrugation disposed adjacent to, and radially outward from, the optical portion.

In still a further aspect of the present invention, there is provided a method for correcting vision of a patient, comprising providing a refractive intraocular lens, wherein the intraocular lens comprises an optical portion and a haptic portion, and wherein the haptic portion is corrugated; forming an incision in an eye of the patient; and inserting the intraocular lens in the eye.

In yet a further aspect of the present invention, a method for correcting vision of a patient comprises the steps of providing a refractive intraocular lens, wherein the intraocular lens comprises an optical portion and a haptic portion, and wherein the haptic portion is corrugated; forming an incision in an eye of the patient; and inserting the intraocular lens in the eye, wherein the eye includes an iris, and the haptic portion is disposed posterior to the iris.

In still another aspect of the present invention, there is provided a method for inserting a refractive intraocular lens in an eye of a patient, the eye including a crystalline lens and an iris, wherein the method comprises deforming a refractive intraocular lens from an extended configuration to a deformed configuration, wherein the intraocular lens comprises an optical portion and a haptic portion, and wherein the haptic portion is corrugated; forming an incision in the eye; introducing the intraocular lens, in the deformed configuration, into the eye via the incision; and positioning the intraocular lens in the eye such that the optical portion is anteriorly spaced from the crystalline lens, and the haptic portion is disposed posterior to the iris.

In yet another aspect of the present invention, there is provided a method for correcting vision of a patient comprising providing a refractive intraocular lens; forming an incision in a cornea of the patient; and inserting the intraocular lens in the cornea, wherein the intraocular lens may comprise an optical portion including a peripheral optic zone having optical power, and an inner non-optic zone surrounded by the peripheral optic zone, wherein the inner non-optic zone has no optical power.

These and other features, aspects, and advantages of the present invention will become better understood with reference to the following drawings, description, and claims.

BRIEF DESCRIPTION OF THE DRAWINGS

FIG. 3A is a plan view of a corrugated IOL in a relaxed configuration, according to another embodiment of the present invention;

FIG. 3B is a sectional view of the corrugated IOL of FIG. 3A as seen along the line 3B-3B of FIG. 3A;

FIG. 3C is a sectional view of the corrugated IOL of FIG. 3A as seen along the line 3C-3C of FIG. 3A;

FIG. 3D is a sectional view of the corrugated IOL of FIG. 3A, as may be seen along the line 3C-3C of FIG. 3A, when the IOL adopts a flexed configuration;

FIG. 3E schematically represents a corrugated IOL in a deformed configuration, according to one aspect of the present invention;

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention relates to refractive intraocular lenses (IOLs) for insertion in an eye and to methods for correction of a visual deficiency of a patient. The present invention also relates to a method for inserting a deformable IOL in a patient's eye via a small incision in the eye.

Unlike prior art IOLs, which are retained against the anterior of the iris by structures that penetrate or grasp the iris tissue, IOLs of the present invention may comprise a corrugated haptic portion for facilitating positioning and retention of the IOL at various locations within the eye. In further contrast to prior art IOLs that have protrusions for spacing the prior art IOL from the crystalline lens, wherein the protrusions may interfere with or restrict deformability of the lens, the IOL of the present invention lacks such protrusions. Instead, IOLs of the present invention may have a domed portion and/or a corrugated haptic portion, such that an optical portion of the IOL is anteriorly spaced from the crystalline lens when the IOL is disposed behind the iris in the posterior chamber of the eye.

In further contrast to the prior art, in some embodiments of the present invention, an IOL optical portion may have a doughnut-like configuration including a peripheral optic-zone and an inner non-optic zone. In alternative embodiments of the present invention, the doughnut-like optical portion may either lack a haptic portion, or may be surrounded by a haptic portion.

In still further contrast to prior art IOLs that have one or more openings for fluid flow within the optical portion, and which may interfere with the optical characteristics of the prior art IOL, IOLs of the present invention may include at least one irrigation channel disposed entirely within the haptic portion to allow passage of aqueous humor therethrough.

Figure 1A:
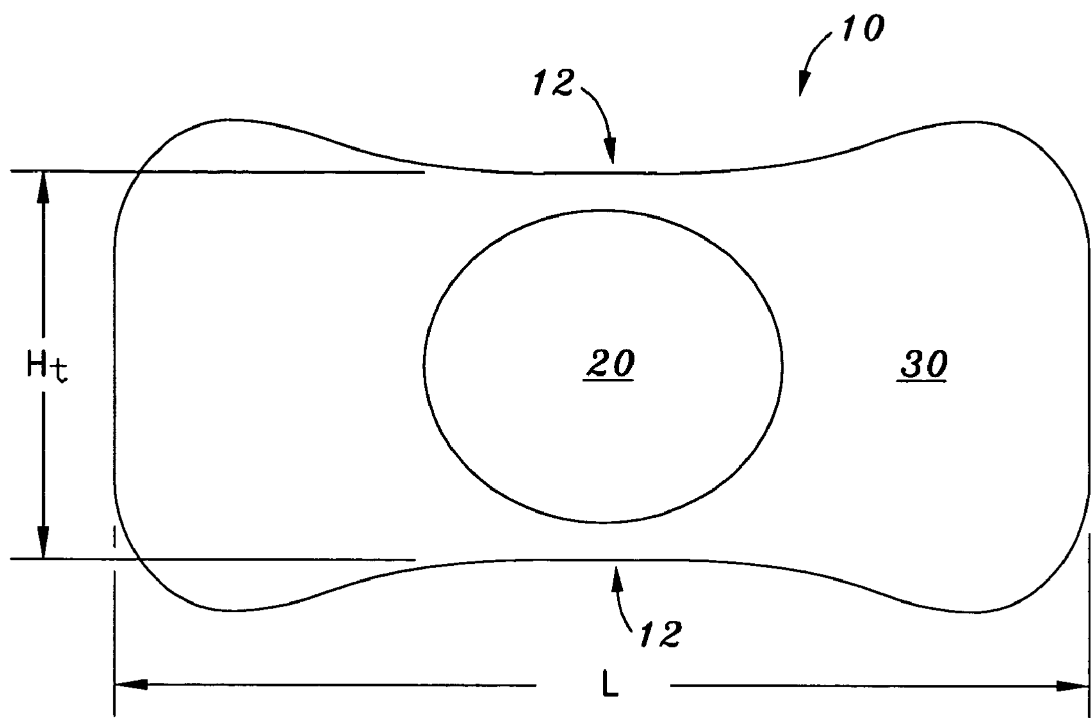
FIG. 1A is a plan view of a corrugated IOL, according to the present invention.

FIG. 1A is a plan view of an IOL 10, according to the present invention. IOL 10 may comprise an optic or optical portion 20. Optical portion 20 may be disposed at a central or inner location of IOL 10. Optical portion 20 is not restricted to the configuration shown in the drawings, but may have various shapes, such as circular or oval, wherein optical portion 20 may be elongated in the horizontal direction or x axis (or shortened in the vertical direction or y axis). In some embodiments, optical portion 20 may have a doughnut-like configuration (see, for example, FIG. 1B).

The optical characteristics of optical portion 20 may be selected for correcting various visual deficiencies, including without limitation: myopia (short sightedness, hypermetropia (long sightedness), and astigmatism. As an example, optical portion 20 may have a diopter power or value in the range of from +15 to −30. Optical portion 20 may be customized for a particular patient to provide optical characteristics to correct a specific visual defect of a patient. Optical portion 20 may be multi-focal. IOL 10 may also be provided as an off-the-shelf unit with pre-determined optical characteristics.

Again with reference to FIG. 1A, IOL 10 may further comprise a haptic or haptic portion 30. Haptic portion 30 may surround optical portion 20. Haptic portion 30 may be corrugated. Haptic portion 30 may vary in the number and configuration of corrugations (see, for example, FIGS. 2A-4B). Haptic portion 30 may be adapted for supporting optical portion 20, and for holding IOL 10 in a desired position in the eye. For example, haptic portion 30 may be adapted for holding IOL 10 behind, or posterior to, the iris of the eye, such that optical portion 20 is spaced anteriorly from the crystalline lens of the eye (see, for example, FIGS. 5A-B, -6). Following insertion of IOL in an eye of a patient, the periphery of haptic portion 30 may contact the perimeter of the posterior chamber 116 (see, e.g., FIGS. 5A-B) of the eye. The periphery of haptic portion 30 may be entire, as shown in FIG. 1A, or in alternative embodiments, haptic portion 30 may have peripheral tabs 38*a-d* (see, for example, FIGS. 2A-C). IOL 10 may further include a tapered portion 12 of haptic portion 30 at a location adjacent to optical portion 20. Haptic portion 30 may have an overall length (x axis), L, in the range of from about 10 to 12 mm, and a height (y axis) at tapered portion 12, $H_t$, in the range of from about 5 to 6.5 mm. The ratio of length, L to height, Ht may typically be in the range of from about 1.5 to about 2.5

Haptic portion 30 may be pigmented. The pigment may be applied to the surface of haptic portion 30 after formation of haptic portion 30. Alternatively, a pigment may be incorporated into a material from which haptic portion 30 is to be formed, e.g., a molten polymer precursor material, such that the pigment is incorporated within haptic portion 30. Haptic portion 30 may be opaque to visible light and/or ultraviolet light. Haptic portion 30 may include an ultraviolet (UV) blocker. UV blockers are well known in the art. In some embodiments, haptic portion 30 may be non-pigmented, and may be transparent or translucent to visible light. Optical portion 20 may be transparent to visible light and may be non-pigmented.

Optical portion 20 and haptic portion 30 may each comprise a flexible material. IOL 10 may be adapted to be reversibly deformed from an extended configuration, for example, as shown in FIGS. 1A-2C, to a deformed configuration (see FIG. 3E). For example, IOL may be adapted to be deformed by rolling or folding for insertion into the eye of a patient via an incision in the eye. Optical portion 20 and haptic portion 30 may each comprise a biocompatible material such as a silicone, a hydrogel, a urethane, or an acrylic, and the like, or other suitable biocompatible material. Materials which may be used in forming intraocular lenses are generally known in the art, as disclosed, for example, in U.S. Pat. No. 5,217,491, the disclosure of which is incorporated by reference herein.

Figure 1B:
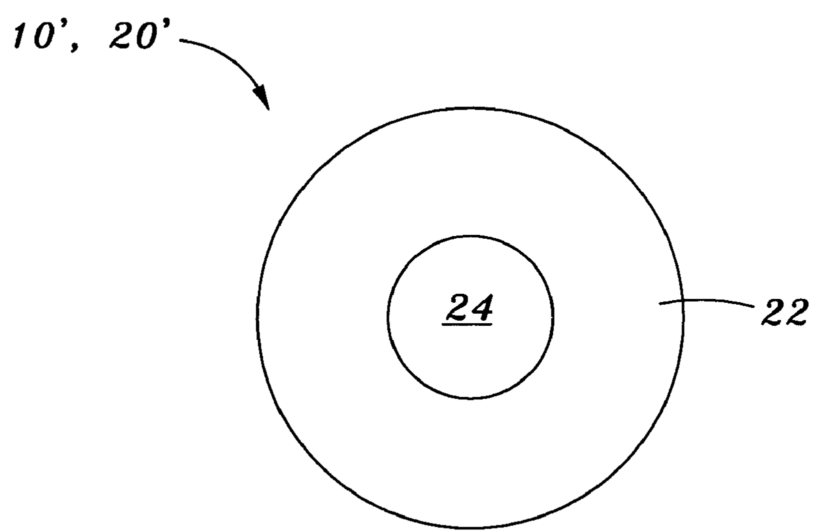
FIG. 1B is a plan view of an optical portion of an IOL, according to another embodiment of the present invention.

FIG. 1B is a plan view of an optical portion 20' for an IOL 10/10", according to another embodiment of the present invention. Optical portion 20' may have a doughnut-like configuration, wherein optical portion 20' may include a peripheral optic zone 22 having optical power. Peripheral optic zone 22 may surround an inner non-optic zone 24 having no optical power. In various embodiments of the present invention, optical portion 20' may be used in combination with various types of haptic portion 30, for example, as described herein with reference to FIGS. 1A, and 2A-4B. As an example, optical portion 20' may be combined with, or surrounded by, a haptic portion 30 having one or more corrugations 34.

Again with reference to FIG. 1B, in alternative embodiments of the present invention, optical portion 20' may be used without a haptic portion (not shown in FIG. 1B). That is to say, an IOL 10" may consist of, or consist essentially of, optical portion 20'. As an example, an IOL 10" lacking a haptic portion may be inserted within the cornea of a patient for vision correction of the patient (see, for example, FIG. 6D). IOL 10/10" including optical portion 20' may be deformable for facile insertion in an eye of the patient, e.g., within a corneal pocket or beneath a corneal flap.

Figure 2A:
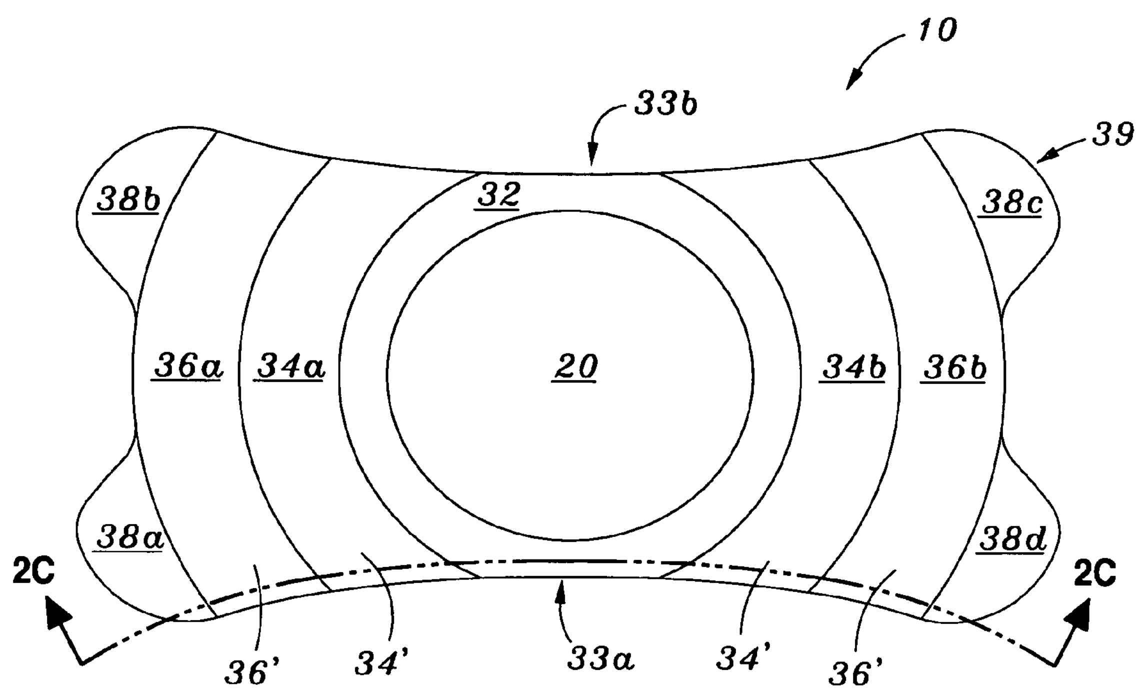
FIG. 2A is another plan view of a corrugated IOL, according to an embodiment of the present invention.
Figure 2C:
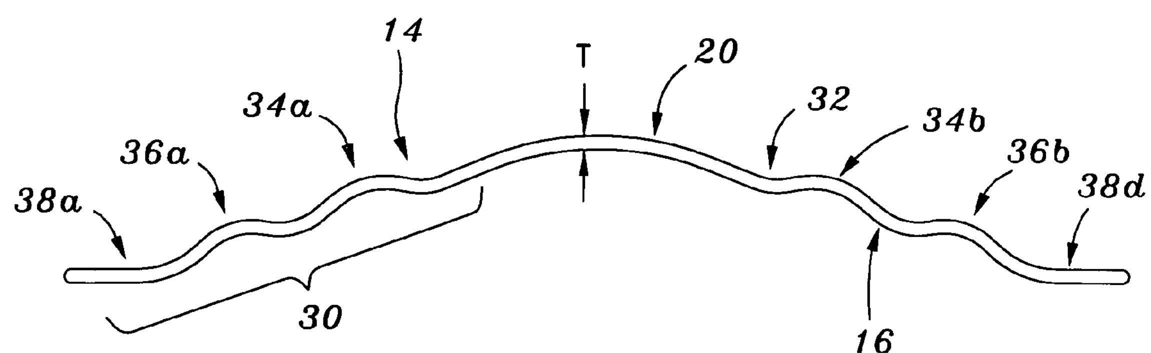
FIG. 2C is a side view of the corrugated IOL of FIGS. 2A-B as taken along the line 2C-2C of FIG. 2A.
Figure 2B:
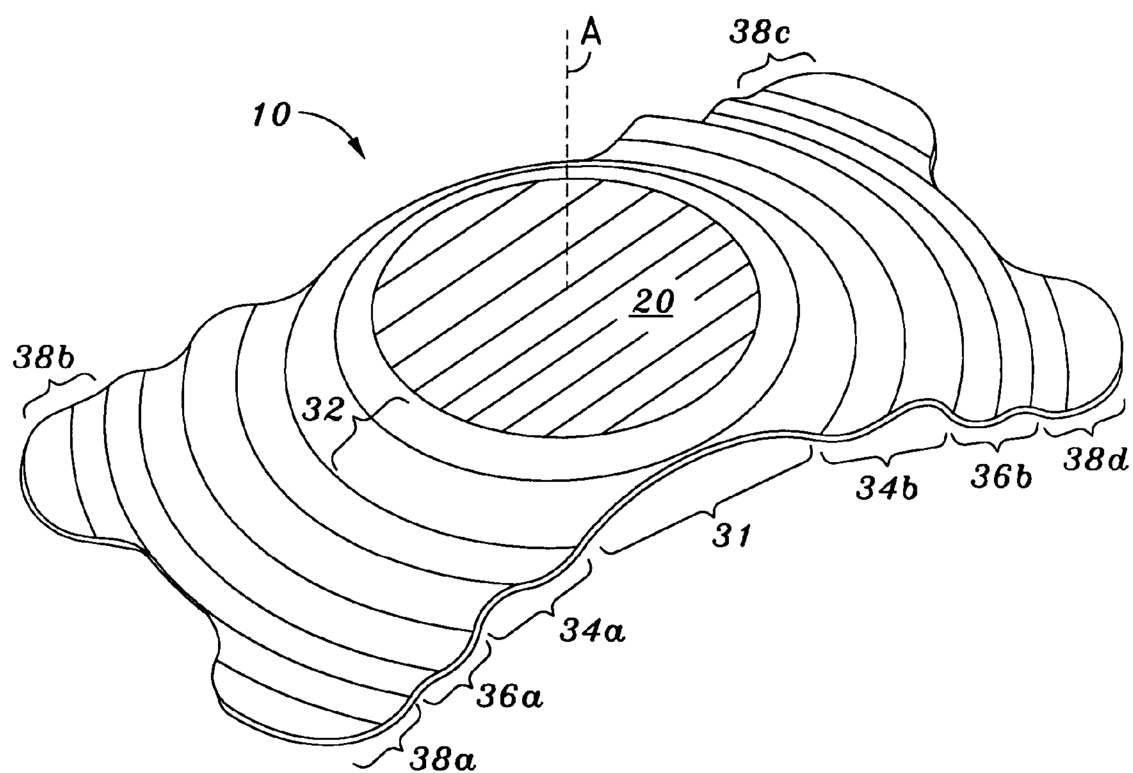
FIG. 2B is a perspective view of the corrugated IOL of FIG. 2A.

FIG. 2A is a plan view of a corrugated IOL 10, according to an embodiment of the present invention. With reference to FIGS. 2A-C, IOL 10 may include optical portion 20, which may be centrally located within IOL 10, essentially as described with reference to FIG. 1A. IOL 10 may further include an annular portion 32 disposed adjacent to, and radially outward from, optical portion 20. Annular portion 32 may encircle optical portion 20. Annular portion 32 may support optical portion 20 such that optical portion 20 is axially spaced from radially outer regions of haptic portion 30, e.g., tabs 38*a-d*. Annular portion 32 may be receded at first and second receded portions 33*a*, 33*b*, which may be disposed diametrically opposite each other. First and second receded portions 33*a*, 33*b* may partially define tapered portion 12 (FIG. 1A).

IOL 10 may further include a first inner arcuate corrugation 34*a* and a second inner arcuate corrugation 34*b* disposed adjacent to, and radially outward from, annular portion 32. As shown in FIG. 2C, haptic portion 30 may have an anterior (or upper) surface 14 and a posterior (or lower) surface 16. First inner arcuate corrugation 34*a* and second inner arcuate corrugation 34*b* may jointly form an inner partial annulus 34'. IOL 10 may still further include a first outer arcuate corrugation 36*a* and a second outer arcuate corrugation 36*b* disposed adjacent to, and radially outward from, inner partial annulus 34'. Both anterior surface 14 and posterior surface 16 of haptic portion 30 may be corrugated, for example, due to first outer arcuate corrugation 36*a* and second outer arcuate corrugation 36*b*.

First outer arcuate corrugation 36*a* and second outer arcuate corrugation 36*b* may jointly form an outer partial annulus 36'. First and second inner arcuate corrugations 34*a*, 34*b* and first and second outer arcuate corrugations 36*a*, 36*b* may be concentric with optical portion 20. Other numbers of corrugations for haptic portion 30 are also within the scope of the invention. Typically, the number of corrugations within haptic portion 30 may be in the range of from 1 to about 5. In general, a larger number of corrugations of haptic portion 30 may lead to increased flexibility and increased deformability in the horizontal direction (x axis). Further, haptic portion 30 may have corrugations (e.g., corrugations 34*a'*, 36*a'*, see FIG. 4A) oriented in directions other than those shown in FIGS. 2A-C.

Corrugation of haptic portion 30 may provide increased rigidity of IOL 30, particularly in the z direction (FIG. 2C), for a given material of a particular thickness and flexibility. Corrugations 34*a-b*, 36*a-b* may be grasped by the surgeon during insertion of IOL in an eye of a patient, and may allow improved maneuverability during positioning of IOL 10 in the eye. Haptic portion 30 may deform, or fold, along one or more corrugations during manipulation of IOL 10 during insertion of IOL 10 in the eye. Increased rigidity of haptic portion 30 may provide improved retention of IOL 10 in a desired intraocular location, and may promote maintenance of a gap, $D_L$ (FIG. 5B) between IOL 10 and crystalline lens 102. Deformation of IOL 10 allows insertion of IOL 10 into the eye of a patient via a small (e.g., about 3 mm) incision. Corrugation of haptic portion 30 may cause IOL 10 to behave like a spring when distorted, for example, from a relaxed configuration (see, for example, FIGS. 2A-C, 3A-C) to a flexed configuration (e.g., FIG. 3D). Flexure of IOL 10 may be caused by forces applied in the x direction, and towards the center of IOL 10, e.g., due to contact of the periphery of haptic portion 30 with the perimeter of the posterior chamber 116 of the eye (e.g., FIG. 6A) or other intraocular structures. Corrugation of haptic portion 30 and its ability to flex may allow IOL 10 to be provided in a single size that fits at least 90% of all human patients. The term "size" as used here may denote a length and height of haptic portion 30. For an IOL 10 of a given size, the amount or degree of flexure of IOL 10, when inserted in the eye, may decrease with increasing size of the eye. Typically, IOL 10 may be sized so as to undergo at least some degree of flexure when inserted in the eye of a patient. Such flexure may promote retention of IOL 10 at a particular intraocular location. In contrast to prior art or conventional IOLs having a planar or non-corrugated haptic, IOL 10 of the invention does not rely on hardware to grasp or penetrate ocular tissues at a particular location in relation to the crystalline lens.

IOL 10 may still further include a plurality of tabs 38*a-d*. Tabs 38*a-d* may be disposed peripherally on haptic portion 30. Each of tabs 38*a-d* may be adapted for being bent with respect to regions of haptic portion 30 located radially inward from tabs 38*a-d*. For example, each of tabs 38*a-d* may be bent when IOL 10 is inserted in the posterior chamber of the eye (see, for example, FIG. 5). Each of tabs 38*a-d* may have a rounded or curvilinear periphery or tab edge 39.

FIG. 2B is a perspective view of corrugated IOL 10 of FIG. 2A, indicating an axis A, which may correspond to an optical axis of IOL 10 or to a central point of optical portion 20. Optical portion 20 and annular portion 32 may jointly define a domed portion 31. Domed portion 31 may be axially spaced from inner partial annulus 34', which in turn may be axially spaced from outer partial annulus 36', which in turn may be axially spaced from tabs 38*a-d*.

FIG. 2C is a side view of the corrugated IOL 10 of FIGS. 2A-B, showing the contours of haptic portion 30 along the line 2C-2C of FIG. 2A, including first and second inner arcuate corrugations 34*a*, 34*b* disposed adjacent to, and radially outward from, annular portion 32; as well as first and second outer arcuate corrugations 36*a*, 36*b* disposed adjacent to, and radially outward from first and second inner arcuate corrugations 34*a*, 34*b*; and tabs 38*a-d* disposed adjacent to, and radially outward from, first and second outer arcuate corrugations 36*a*, 36*b*. Haptic portion 30 may have a thickness (z axis), T, typically in the range of from about 50 to 200 microns, usually from about 75 to 200 microns, and often from about 75 to 150 microns. When IOL 10 is in the relaxed state, first and second inner arcuate corrugations 34*a*, 34*b* may have an axial distance (or height) typically in the range of from about 400 to 1000 microns, usually from about 500 to 900 microns, and often from about 700 to 800 microns; while first and second outer arcuate corrugations 36*a*, 36*b* may have an axial distance (or height) typically in the range of from about 250 to 700 microns, usually from about 300 to 550 microns, and often from about 300 to 400 microns. IOL 10 may have an overall axial distance, or height, from optical portion 20 to tabs 38*a-d*, typically in the range of from about 1700 to 2100 microns, usually from about 1800 to 2000 microns, and often about 1900 microns.

FIG. 3A is a plan view of a corrugated IOL 10, according to another embodiment of the present invention. FIG. 3B is a sectional view of IOL 10 as seen along the line 3B-3B of FIG. 3A, and FIG. 3C is a sectional view of IOL 10 as seen along the line 3C-3C of FIG. 3A. With reference to FIGS. 3A-C, IOL 10 may include various elements, features, and characteristics as described hereinabove with reference to FIGS. 1A-2C. For example, IOL 10 of FIGS. 3A-C may include an inner optical portion 20 and an outer haptic portion 30.

Each of optical portion 20 and haptic portion 30 may comprise a flexible material, and IOL 10 may be readily deformable, e.g., for insertion through an incision in an eye. Haptic portion 30 may encircle optical portion 20, and haptic portion 30 may support IOL 10 when positioned in an eye of a patient during a surgical procedure for the correction of a visual deficiency (see, for example, FIGS. 5A-B, 6, 7A-B).

IOL 10 may be seen in FIGS. 3A-C in a relaxed configuration. With reference to FIGS. 3B and 3C, it can be readily appreciated that, when IOL 10 is in the relaxed (e.g., non-deformed) configuration, optical portion 20 may be axially spaced (relative to axis A, FIG. 2B) from structures of haptic portion 30, such as tabs 38*a-d*.

IOL 10 may be flexible and may also temporarily and reversibly adopt a deformed configuration (see FIG. 3E), for example, by folding or rolling IOL 10, for insertion through an incision in the eye of a patient, wherein the size of the incision may be minimized, e.g., to a length typically in the range of from about 2.8 to 3.2 mm.

IOL 10 may still further adopt a flexed configuration, for example, when positioned behind (posterior to) the iris of an eye (see FIG. 5), wherein flexure of haptic portion 30 caused, for example by positioning IOL 10 between intraocular structures, may cause haptic portion 30 to exert a force against an intraocular structure, such as the posterior surface of the iris. The rigidity of haptic portion 30, and hence the force exerted thereby, may be increased by first and second inner arcuate corrugations 34*a*, 34*b* and first and second outer arcuate corrugations 36*a*, 36*b*, as compared with a non-corrugated haptic of similar composition and dimensions. Accordingly, in the flexed configuration of IOL 10, haptic portion 30 may exert a greater force against an intraocular structure, and have improved retention within an intraocular location, as compared with a conventional, non-corrugated IOL.

With reference to FIG. 3A, haptic portion 30 may have a width at tapered portion 12, $H_t$, typically in the range of from about 5 to 6.5 mm, usually from about 5.2 to 6.0 mm, and often from about 5.5 to 5.9 mm. IOL 10 may have a first edge 30*a* and a second edge 30*b*. Each of first edge 30*a* and second edge 30*b* may have an arcuate shape in plan view (e.g., FIG. 3A), having a radius of curvature $R_h$. The value of $R_h$ may be typically in the range of from about 15 to 20 mm, usually from about 16 to 19 mm, and often from about 17 to 18 mm. Haptic portion 30 may have an overall diameter, $D_h$, as measured diametrically from an edge of tab 38*a* to an edge of tab 38*c*, typically in the range of from about 11.5 to 14.5 mm, usually from about 12 to 14 mm, and often from about 12.5 to 13.5 mm. Optical portion 20 may have a diameter, $D_o$, typically in the range of from about 4 to 5 mm, usually from about 4.2 to 4.9 mm, and often from about 4.5 to 4.7 mm.

Again with reference to FIGS. 3A-C, IOL 10 may further include at least one irrigation channel 40. Each irrigation channel 40 may be adapted to allow the passage of a fluid therethrough. For example, following insertion of IOL 10 in an eye of a patient, each irrigation channel 40 may allow the passage of aqueous humor therethrough. In some embodiments, IOL 10 may have at least two irrigation channels 40. Irrigation channels 40 may be radially disposed with respect to optical portion 20. Irrigation channels 40 may be disposed diametrically opposite each other with respect to optical portion 20. Irrigation channels 40 may be elongate, and may have a width, $W_c$, typically in the range of from about 0.2 to 0.5 mm, usually from about 0.25 to 0.45 mm, and often from about 0.3 to 0.4 mm. Irrigation channels 40 may be disposed entirely within haptic portion 30. That is to say, optical portion 20 may be free from irrigation channels 40. As a non-limiting example, irrigation channels 40 may extend radially outward from annular portion 32 to outer partial annulus 36'. As shown in FIG. 3A, a total of six (6) irrigation channels 40 may be disposed radially with respect to optical portion 20; however, other numbers and arrangements for irrigation channels 40 are also within the scope of the invention.

IOL 10 may further include at least one orientation label for indicating an orientation of IOL 10. As a result, orientation of IOL 10 may be readily discerned during insertion of IOL 10 in the eye of a patient. As shown in FIG. 3A, IOL 10 may include a pair of orientation labels 42*a*, 42*b*, wherein orientation labels 42*a*, 42*b* may be disposed diametrically opposite each other. Orientation labels 42*a*, 42*b* may be disposed within tabs 38*b*, 38*d*. Orientation labels 42*a*, 42*b* may be in the form of an indented region of haptic portion 30, a colored region of haptic portion 30, and the like, which may be readily visualized, e.g., by a surgeon. Thus, if the surgeon turns IOL 10 over, i.e., changes the orientation of IOL 10, orientation labels 42*a*, 42*b* "shift" from, e.g., upper left and lower right portions of IOL 10 to upper right and lower left portions of IOL 10, thereby indicating the changed orientation of IOL 10.

FIG. 3D is a sectional view of IOL 10 of FIG. 3A, as may be seen along the line 3C-3C of FIG. 3A, when the IOL adopts a flexed configuration. The elements shown in FIG. 3D correspond to those shown and described with respect to FIGS. 3A-C, although the configuration of the various elements, including domed portion 31; first and second inner arcuate corrugations 34*a*, 34*b*; first and second outer arcuate corrugations 36*a*, 36*b*; and tabs 38*a-d*, with respect to each other may be changed. In the flexed configuration, IOL 10 may act as a spring to facilitate its retention at a given intraocular location. IOL 10 may adopt a range of flexed configurations, for example, depending on the direction and magnitude of forces applied to haptic portion. Such forces may depend on the geometry of an eye in which IOL 10 may be inserted, as well as the geometry and composition of IOL 10. Accordingly, the invention is by no means limited to flexure in configurations shown in the drawings.

With reference to FIG. 3E, IOL 10 may adopt a deformed configuration. Deformation of IOL 10 is schematically represented in FIG. 3E. It is to be understood that other deformed configurations are also possible for IOL 10 under the invention. For example, IOL 10 may adopt a folded configuration, a rolled configuration, or a partly rolled and partly folded configuration. Various deformed configurations of an intraocular lens are disclosed by Mazzocco in U.S. Pat. No. 4,573,998, the disclosure of which is incorporated by reference herein in its entirety. In some embodiments of the invention, IOL 10 may be deformed during passage through a small incision (e.g., having a length of from about 2.8 to 3.3 mm) in a procedure for insertion of IOL 10 in an eye of a patient.

Figure 4A:
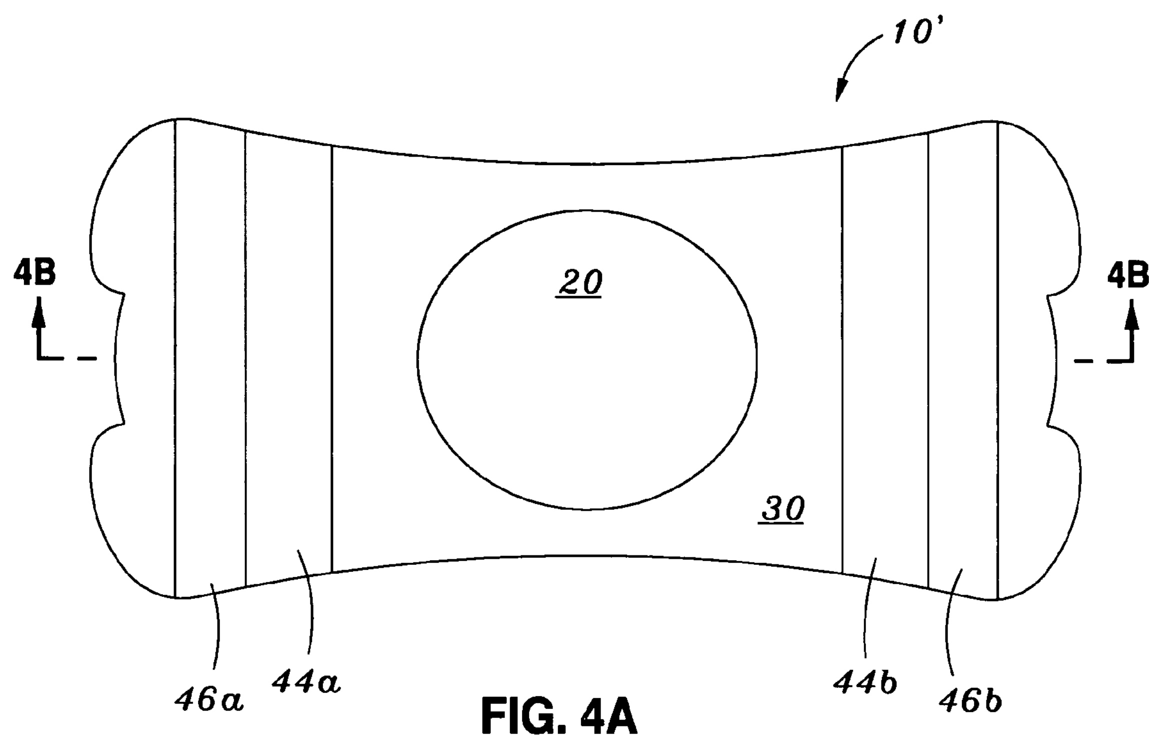
FIG. 4A is a plan view of a corrugated IOL, according to another embodiment of the present invention.
Figure 4B:
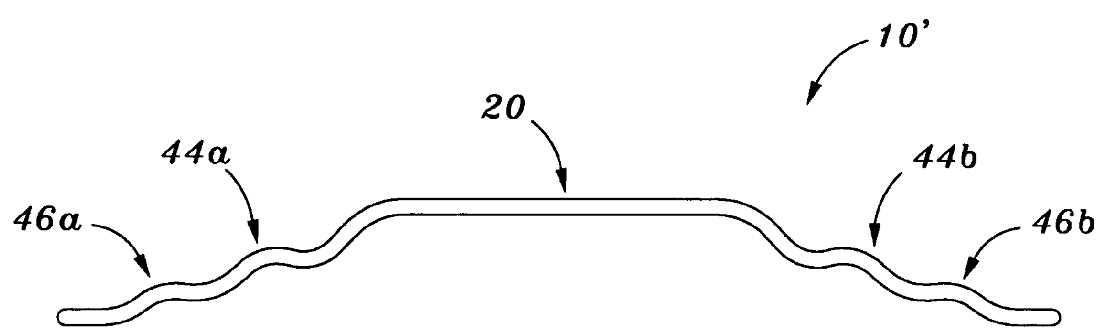
FIG. 4B is a sectional view of the corrugated IOL of FIG. 4A taken along the line 4B-4B of FIG. 4A.

FIG. 4A is a plan view of a corrugated IOL 10', according to another embodiment of the present invention, and FIG. 4B is a sectional view of the corrugated IOL 10' of FIG. 4A taken along the line 4B-4B of FIG. 4A. With reference to FIGS. 4A-B, IOL 10' may include haptic portion 30 and optical portion 20, which may be centrally located within IOL 10', essentially as described hereinabove, e.g., with reference to FIGS. 1A and 2A-C. IOL 10' may further include first inner linear corrugation 44*a* and second inner linear corrugation 44*b*, wherein first and second inner linear corrugations 44*a-b* are oriented in the vertical direction (y axis). IOL 10' may still further include first and second outer linear corrugations 46*a-b*, also oriented in the vertical direction, and disposed distal to first and second inner linear corrugations 44*a-b* with respect to an optical axis of IOL 10' (corresponding to axis A, FIG. 2B). However, the invention is not limited to the number or arrangement of corrugations shown in the drawings, but rather, other numbers and arrangements for corrugations of haptic portion 30 are also within the scope of the invention.

Figure 5A:
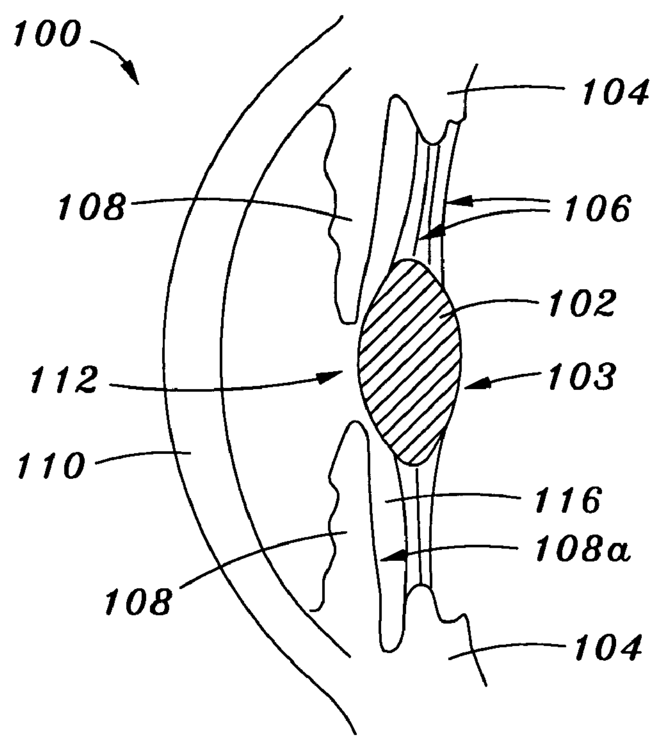
FIG. 5A is a sectional view of the anterior portion of an eye.
Figure 5B:
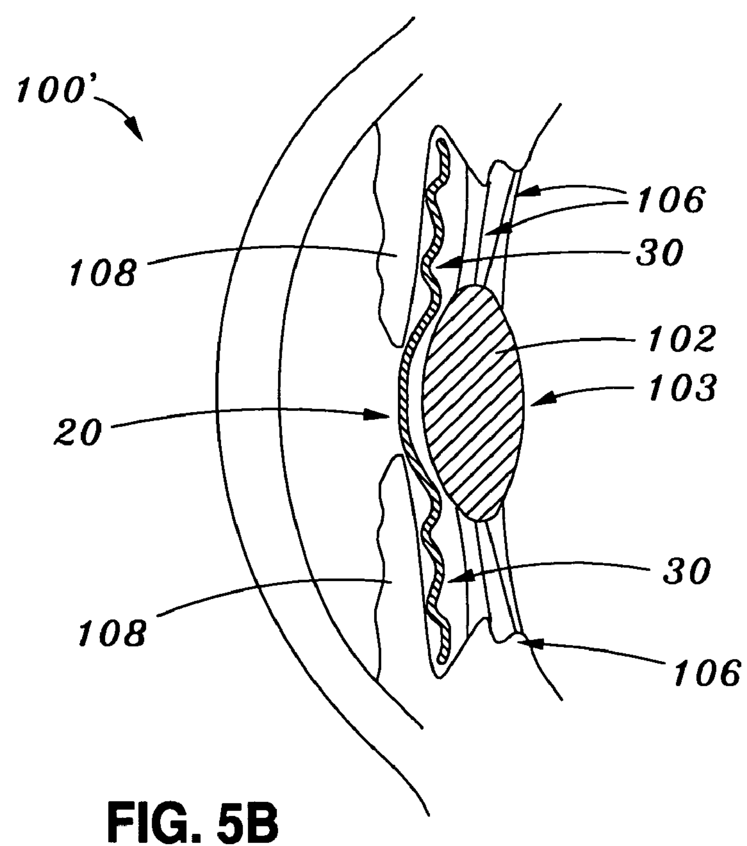
FIG. 5B is a sectional view of the anterior portion of an eye having a corrugated IOL disposed in the eye, according to another embodiment of the invention.

With reference to FIGS. 5A-B, FIG. 5A is a sectional view of the anterior portion of an eye 100, which includes a natural crystalline lens 102 suspended from a ciliary body 104 via zonular fibers 106. The eye 100 further includes an iris 108 located anterior to crystalline lens 102, and a cornea 110 located anterior to iris 108. The crystalline lens 102 is encased within a capsule 103. The iris 108 is an annular structure that defines an aperture or pupil 112. The iris 108 has a posterior surface 108*a*. Eye 100 further includes an anterior chamber 114 located anterior to iris 108, and a posterior chamber 116 located posterior to iris 108. Anterior chamber 114 and posterior chamber 116 may each contain aqueous humor (not shown).

FIG. 5B is a sectional view of the anterior portion of an eye 100' having a corrugated IOL 10 disposed in the eye, according to an embodiment of the present invention. IOL 10 shown in FIG. 5B may have various features, characteristics, and elements in common with embodiments described with reference to FIGS. 1A-3C. Thus, IOL 10 may have a central optical portion 20 and an outer haptic portion 30. IOL 10 may be disposed in posterior chamber 116. Haptic portion 30 may be disposed adjacent, and posterior, to iris 108. One or more corrugations of haptic portion 30 may be adapted for contacting a posterior surface 108*a* of iris 108. IOL 10 may be in a flexed configuration when disposed in posterior chamber 116. The flexed configuration may promote retention of IOL 10 in eye 100, e.g., by contact between haptic portion 30 and one or more intraocular structures, such as one or more of the iris 108, the ciliary body 104, a peripheral (non-optical) region of the crystalline lens 102, and the zonular fibers 106.

Figure 5C:
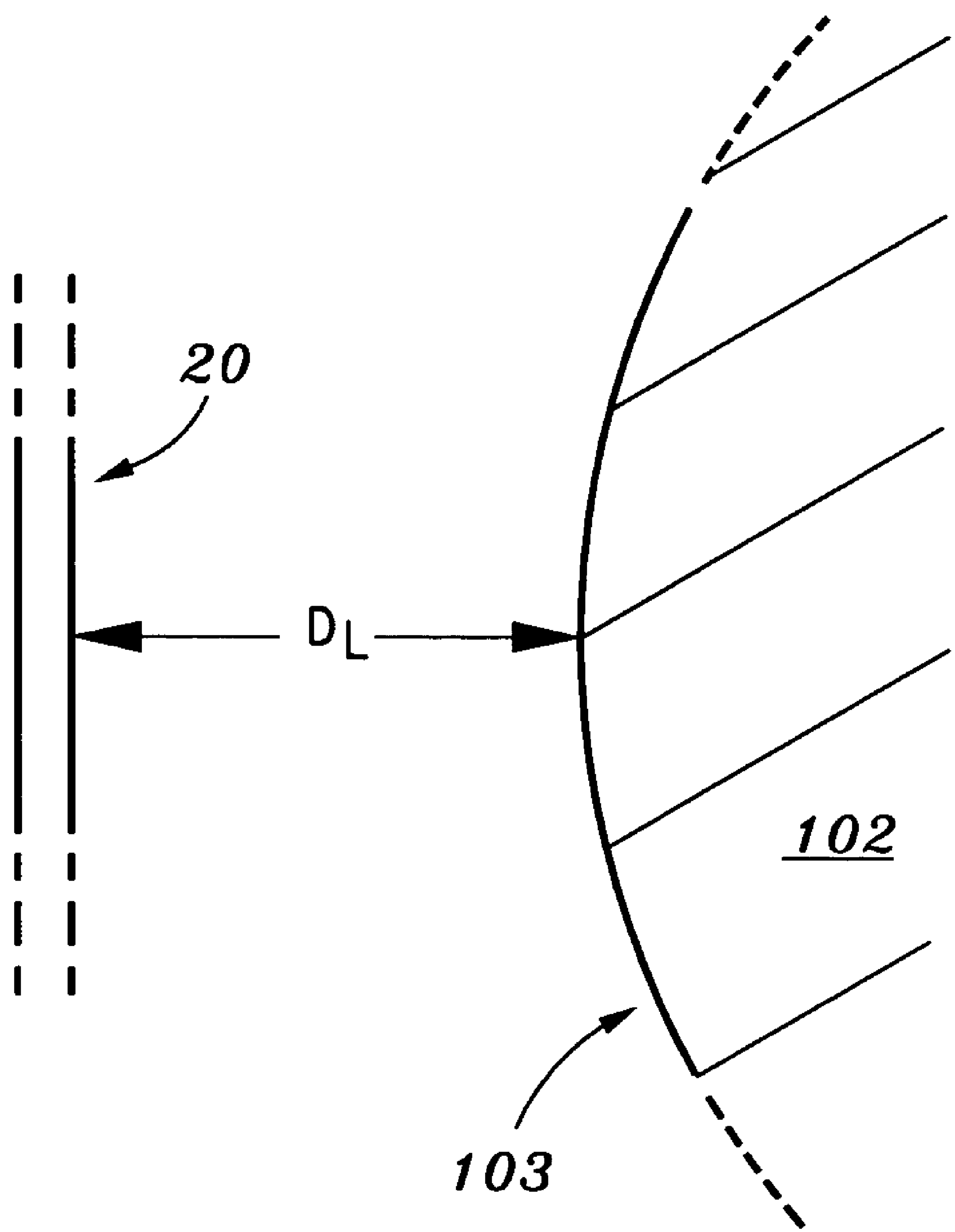
FIG. 5C is an enlarged view showing a gap between an optical portion of the IOL and the crystalline lens of the eye of FIG. 5B.

FIG. 5C is an enlarged view showing a gap between an optical portion of the IOL and the crystalline lens of the eye of FIG. 5B. IOL 10 may be disposed in posterior chamber 116 such that optical portion 20 is spaced anteriorly from crystalline lens 102, by a gap or distance, $D_L$, wherein $D_L$ may typically be in the range of from about 50 to 500 microns, usually from about 100 to 350 microns, and often from about 10 to 200 microns. Optical portion 30 may have optical characteristics that provide correction of a deficiency, such as myopia (short sightedness), hypermetropia (long sightedness), or astigmatism of eye 100'. It is to be understood that the present invention is not limited to treatment of these defects, and that treatment of other eye conditions is also within the scope of the invention. In alternative embodiments of the present invention (not shown), IOL 10 may be disposed in anterior chamber 114 of eye 100/100'.

Figure 6A:
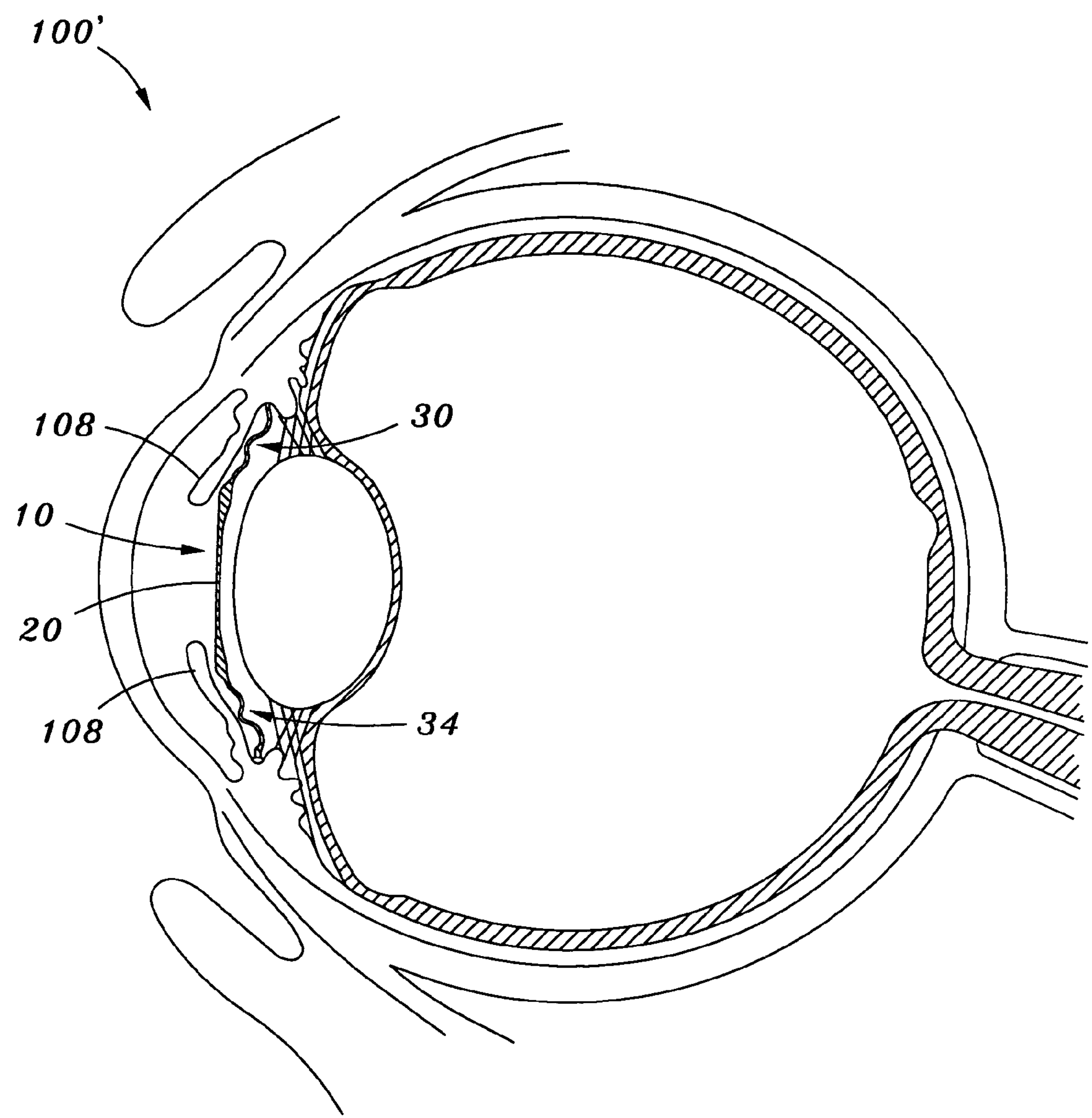
FIG. 6A is a sectional view of an eye having a corrugated IOL disposed in the eye, according to another embodiment of the invention.

FIG. 6A is a sectional view of an eye 100' having a corrugated IOL 10 disposed therein, according to another embodiment of the invention. IOL 10 shown in FIG. 6A may also have various features, characteristics, and elements in common with embodiments described with reference to FIGS. 1A-3C. Thus, IOL 10 may include optical portion 20 and haptic portion 30. IOL 10 may be disposed posterior to iris 108. Haptic portion 30 may include one or more corrugations 34 which may be disposed adjacent posterior surface 108*a* of iris 108. As shown, IOL 10 may be disposed in eye 100' such that IOL 10 avoids contact with crystalline lens 102, thereby avoiding damage to crystalline lens 102. Spacing of optical portion 20 anterior to crystalline lens 102 may be facilitated by corrugation of haptic portion 30 and by axial displacement of domed portion 31 from outer portions, e.g., tabs 38*a-d*, of haptic portion 30 (see, for example, FIG. 2B). Tabs 38*a-d* may provide four-point contact at the perimeter of the posterior chamber 116, and may help to retain optical portion 20 in a central location anterior to the central, optical portion of the crystalline lens 102. Contact between tabs 38*a-d*, or other point(s) of contact of haptic portion 30, and the perimeter of the posterior chamber 116 of eye 100' may cause flexure of IOL 10, leading to corrugations 34 being pushed against the posterior surface of the iris 108. It should be understood, however, that the invention is not limited to a haptic portion 30 having tabs 38*a-d*. For example, in some embodiments, haptic portion 30 may lack tabs (see FIG. 1A).

Figure 6B:
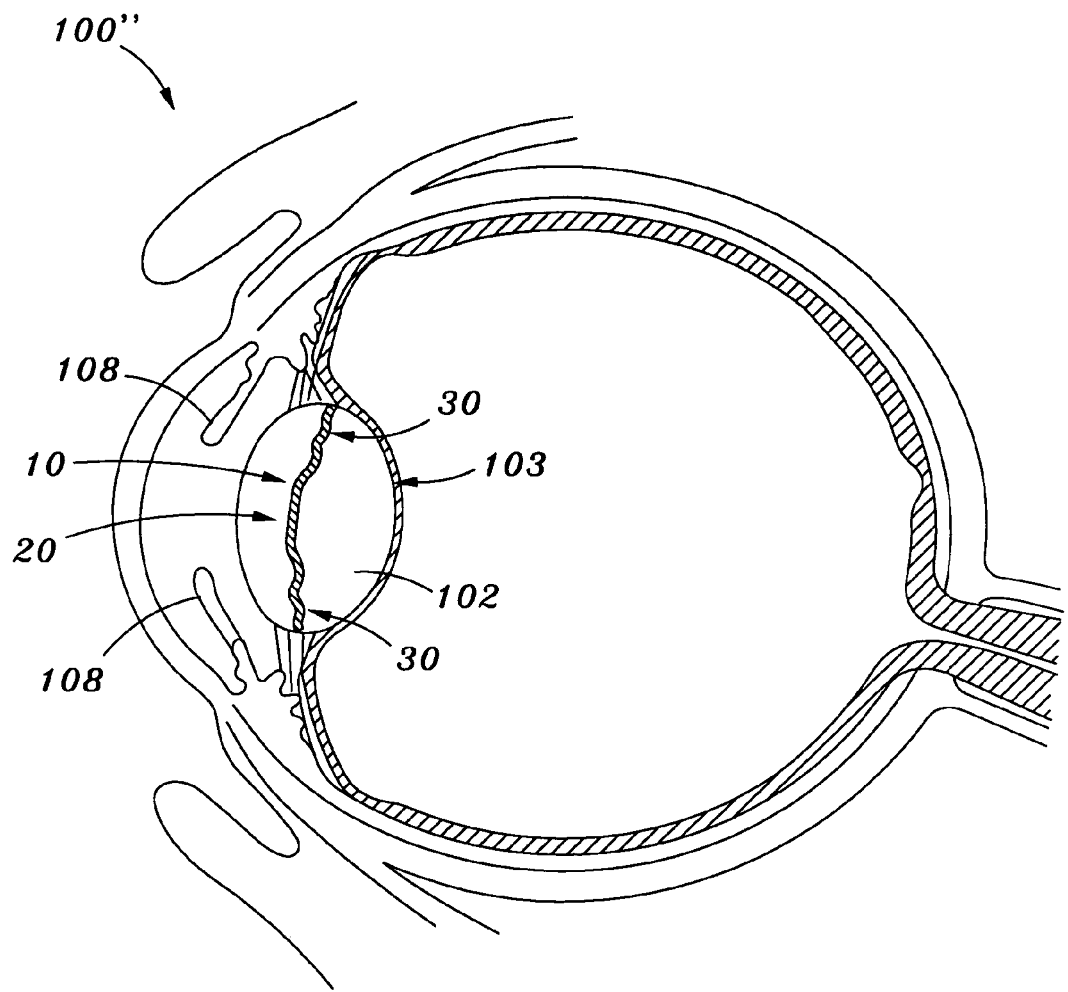
FIG. 6B is a sectional view of an eye having a corrugated IOL disposed within the capsule of the crystalline lens, according to another embodiment of the invention.

FIG. 6B is a sectional view of an eye 100" having a corrugated IOL 10 disposed therein, according to another embodiment of the invention. In the embodiment of the invention shown in FIG. 6B, IOL 10 may be disposed within capsule 103 of crystalline lens 102. As an example, IOL 10 may be inserted within crystalline lens 102 following capsulorrhexis, in which a continuous circular incision may be formed in the anterior of capsule 103 of crystalline lens 102. The capsulorrhexis technique is well known in the art, for example, with respect to cataract surgery. IOL 10 shown in FIG. 6B may also have various features, characteristics, and elements in common with embodiments described hereinabove, e.g., with reference to FIGS. 1A-3C.

Figure 6C:
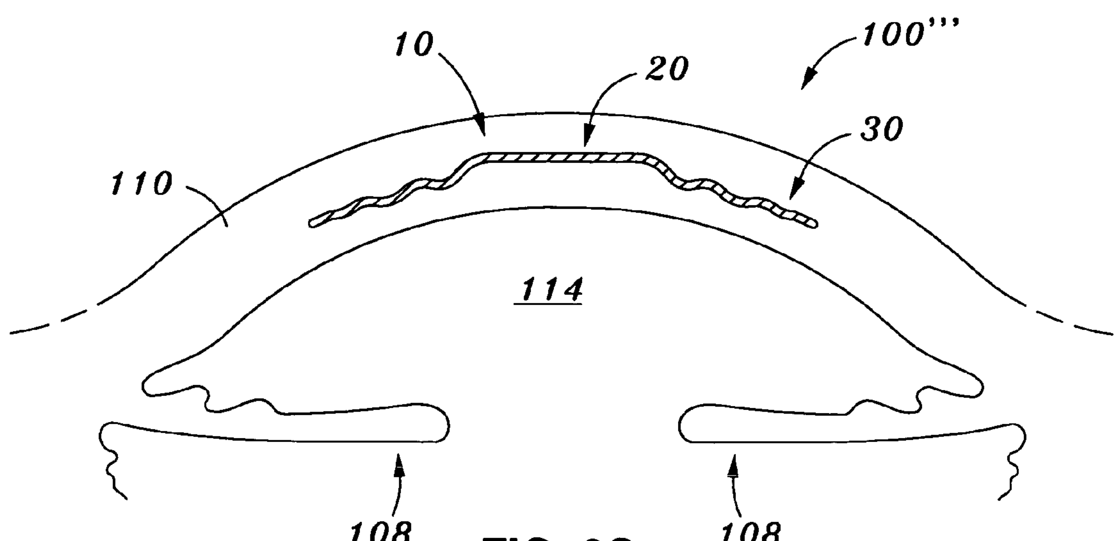
FIG. 6C is a sectional view of the anterior portion of an eye having a corrugated IOL disposed within the cornea of the eye, according to another embodiment of the invention.

FIG. 6C is a sectional view of the anterior portion of an eye 100'" having a corrugated IOL 10 disposed therein, according to another embodiment of the invention. In the embodiment of the invention shown in FIG. 6C, IOL 10 may be disposed within cornea 110 of crystalline lens 102. As an example, IOL 10 may be inserted within cornea 110 following formation of a corneal flap or a corneal pocket, which may be formed, e.g., using a corneal-pocket keratome device as disclosed in U.S. Pat. No. 6,599,305, the disclosure of which is incorporated by reference herein in its entirety. For insertion in cornea 110, IOL 10 may have an opaque haptic portion 30, and/or haptic portion 30 may be located outside the optical zone of the eye 100'", whereby interference with the vision of the patient by haptic portion 30 may be avoided. In an alternative embodiment, the haptic portion may be eliminated, whereby IOL 10/10" may consist essentially of optical portion 20/20' (see, e.g., FIG. 6D). IOL 10 shown in FIG. 6C may also have various features, characteristics, and elements in common with embodiments described hereinabove, e.g., with reference to FIGS. 1A-3C.

Figure 6D:
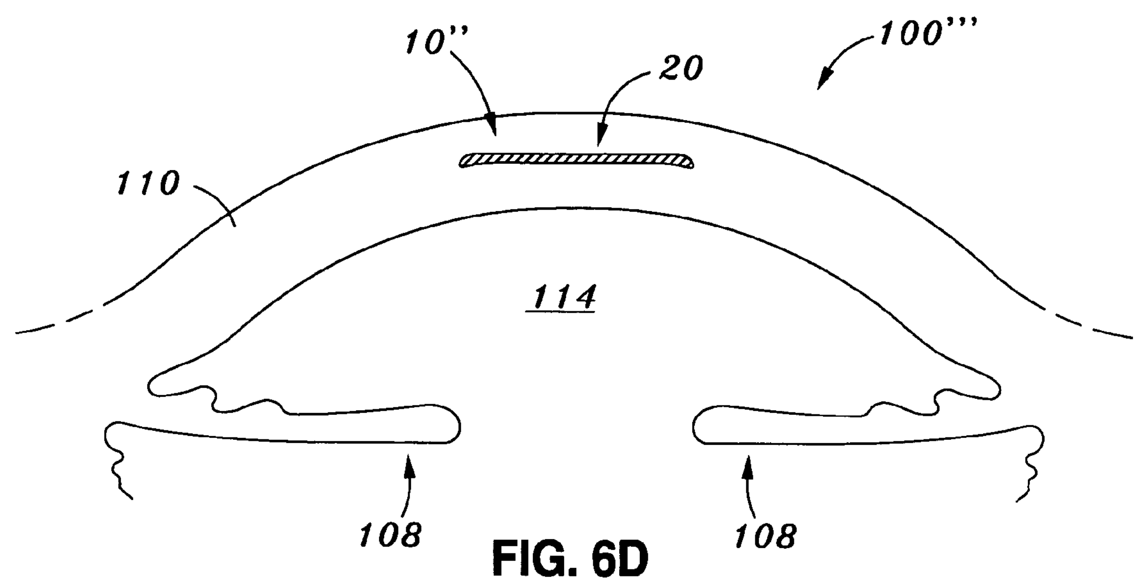
FIG. 6D is a sectional view of the anterior portion of an eye having an IOL disposed within the cornea of the eye, according to another embodiment of the invention.

FIG. 6D is a sectional view of the anterior portion of an eye 100'" having an IOL 10" disposed therein, according to another embodiment of the invention. IOL 10" may comprise an optical portion 20/20'. At least a portion of haptic portion 30 (e.g., FIG. 6C) may be missing or removed in IOL 10". As an example, IOL 10" may have either no haptic portion, or a vestigial haptic portion 30 (FIG. 6C). IOL 10" may be inserted within cornea 110 following formation of a corneal flap or a corneal pocket, for example, as described with reference to FIG. 6C. Optical portion 20/20' in the embodiment of FIG. 6D may have various features, characteristics, and elements in common with other embodiments of the present invention as described hereinabove. For example, an optical portion 20/20' for insertion in cornea 110 may have a doughnut-like configuration comprising a peripheral optic zone 22 having optical power and an inner non-optic zone 24 having no optical power (see, e.g., FIG. 1B).

Figure 6E:
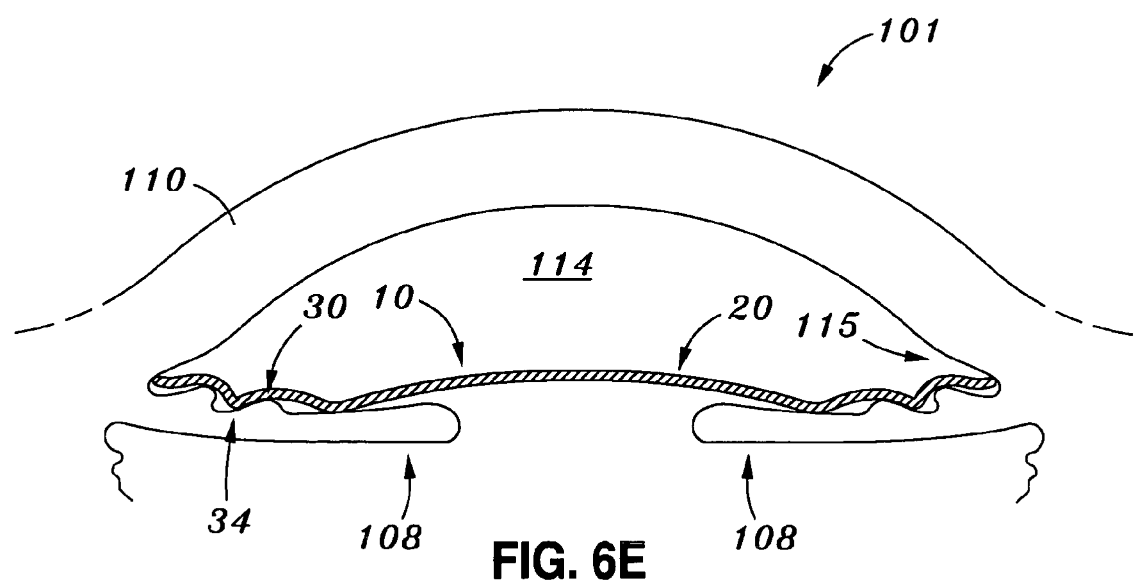
FIG. 6E is a sectional view of the anterior portion of an eye having a corrugated IOL disposed within the anterior chamber of the eye, according to another embodiment of the invention.

FIG. 6E is a sectional view of the anterior portion of an eye 101 having a corrugated IOL 10 disposed within the anterior chamber 114 of the eye 101, according to another embodiment of the invention. IOL 10 may be disposed in the anterior chamber 114 such that corrugations 34 of haptic portion 30 contact the anterior surface of the iris 108. IOL 10 may also be positioned in the anterior chamber 114 of the eye 101 such that peripheral portions (e.g., tabs 38*a-d*, FIG. 2A) of IOL 10 are disposed in the iridocorneal angle 115. Flexure of IOL 10 (see, for example, FIGS. 3B, 3D) may promote retention of IOL 10 in relation to iris 108 as shown in FIG. 6E.

Figure 7A:
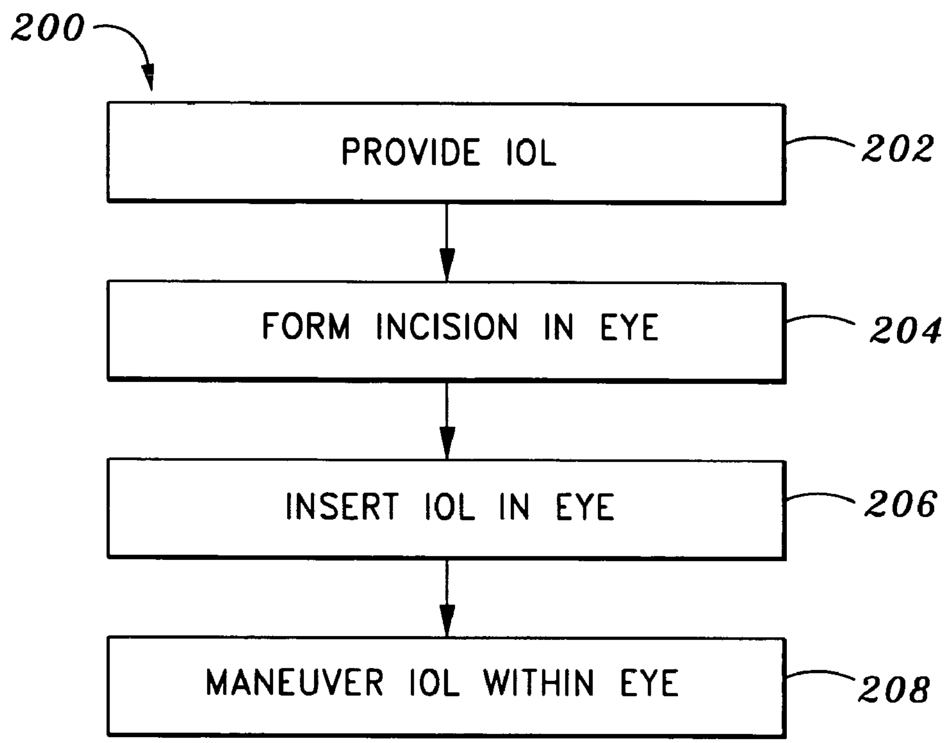
FIG. 7A schematically represents a series of steps involved in a method for correcting vision in a patient, according to another embodiment of the invention.

FIG. 7A schematically represents a series of steps involved in a method 200 for correcting vision in a patient, according to another embodiment of the invention. Methods and injector apparatus for inserting a deformable intraocular lens in an eye of a patient are disclosed in U.S. Pat. Nos. 4,573,998 and 4,702,244 both to Mazzocco, and U.S. Pat. No. 6,106,553 to Feingold, the disclosures of each of which is incorporated by reference herein in their entirety.

Step 202 of method 200 may involve providing an IOL of the present invention. The IOL provided in step 202 may have various features, characteristics, and elements as described for various embodiments of the invention, for example, as described with reference to FIGS. 1A-3C, supra. The IOL may have an optical portion for correcting a particular visual defect in a patient. Such visual defects may include, without limitation, myopia (short sightedness), hypermetropia (long sightedness), and astigmatism. The IOL may have an optical portion having optical characteristics tailored for a particular patient. In some embodiments, the optical portion may comprise an inner non-optic zone with no optical power, and a peripheral optic zone having optical power. In some embodiments, the IOL may further have a haptic portion surrounding the optical portion, wherein the haptic portion may be corrugated (see, e.g., FIGS. 2B-C, 4B, and 5).

Step 204 may involve forming an incision in the eye of the patient for inserting the IOL therethrough. The incision may typically have a length in the range of from about 2.8 to 3.2 mm. The incision may be made in the vicinity of the limbus, or margin, of the cornea.

Step 206 may involve inserting the IOL in the eye. The IOL may be temporarily and reversibly deformed (see, for example, step 302 of method 300) into a deformed or compact configuration prior to step 206. The IOL may be inserted in the eye using an injector, as is known in the art.

Prior to step 206, the iris may be dilated to enlarge the pupil of the eye. The lens may be inserted in step 206 under a suitable viscoelastic material, such as a derivative of methyl cellulose, sodium hyaluronate, and the like. Such viscoelastics may be used to maintain the volume of the posterior or anterior chamber of the eye and for mechanical protection of the endothelium of the cornea during the procedure.

Step 208 may involve maneuvering the IOL in the eye, for example, such that the IOL may be placed in the posterior chamber between the iris and the crystalline lens of the eye, and wherein the optical portion of the IOL is axially aligned with the crystalline lens. Corrugations of the haptic portion of the IOL may facilitate maneuvering the IOL during step 208 by providing rigidity to the IOL, and by allowing the surgeon to grasp the haptic portion by the corrugations.

Step 208 may further involve maneuvering the IOL in the anterior chamber of the eye such that a first side of the haptic portion is deformed to place the first side of the haptic portion posterior to the iris, and thereafter a second side of the haptic portion is deformed to place the second side of the haptic portion posterior to the iris, such that the IOL is disposed in the posterior chamber of the eye. Step 208 may still further involve maneuvering the IOL in the eye such that the IOL adopts a flexed configuration, for example, wherein the periphery of the haptic portion contacts the perimeter of the posterior chamber of the eye. After step 208, the pupil may be contracted, and the viscoelastic material may be removed by suction, as is well known in the art, and thereafter physiological (normal) saline may be added to the posterior and anterior chambers of the eye. In alternative embodiments, the IOL may be inserted in the cornea, within the capsule of the crystalline lens, or in the anterior chamber of the eye (see, for example, FIGS. 6A-E).

Figure 7B:
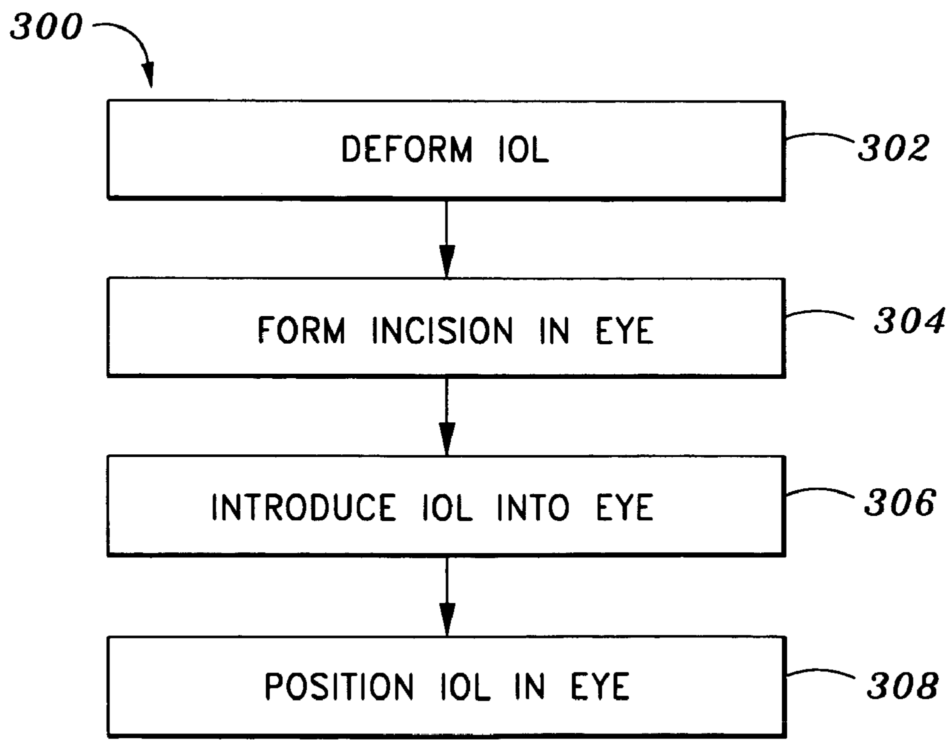
FIG. 7B schematically represents a series of steps involved in a method for inserting a corrugated, deformable IOL in the eye of a patient, according to another embodiment of the invention.

FIG. 7B schematically represents a series of steps involved in a method 300 for inserting a corrugated, deformable IOL in the eye of a patient, according to another embodiment of the invention, wherein step 302 may involve temporarily deforming the IOL preparatory to introducing the IOL into the eye. The IOL may be deformed by rolling, folding, and the like. The IOL of the invention may have prescribed memory characteristics that allow the IOL to return to its original size and configuration after insertion in the eye, while retaining the optical characteristics of the optical portion. Deformation of intraocular lenses is described in U.S. Pat. No. 6,106,553 to Feingold, and U.S. Pat. Nos. 4,573,998 and 4,702,244 both to Mazzocco, the disclosures of each of which is incorporated by reference herein in their entirety. The IOL may be deformed prior to insertion into an IOL injector apparatus, as referred to hereinabove with reference to method 200, FIG. 7A.

Step 304 may involve forming an incision in the eye for introduction of the deformed IOL therethrough. The incision may be formed generally as described hereinabove for step 204 of method 200, with reference to FIG. 7A. By deforming the IOL, the length of the incision may be kept to a length typically in the range of from about 2.8 to 3.2 mm. Step 306 may involve introducing the deformed IOL into the eye, via the incision, using a suitable injector device, e.g., as referred to hereinabove. Injector devices for inserting IOLs in the eye of a patient are generally known in the art. In some embodiments, step 306 may be performed before step 304, and step 304 may involve deforming the IOL as the IOL is inserted through the incision in the eye.

Step 308 may involve positioning the IOL in the eye. The IOL may be positioned in the posterior chamber, generally as described hereinabove with reference to FIG. 7A. For example, the IOL may be positioned such that the haptic portion of the IOL is disposed adjacent the posterior surface of the iris, and the optic portion of the IOL is spaced anteriorly from the crystalline lens. Irrigation channels and/or orientation markers disposed within the haptic portion (see, for example, FIG. 3A) may facilitate positioning the IOL in the eye during step 308.

In alternative embodiments, step 308 may involve positioning the IOL in the eye at locations other than the posterior chamber anterior to the crystalline lens. For example, the IOL may be positioned within the capsule of the crystalline lens (see, e.g., FIG. 6B), in the cornea (see, e.g., FIGS. 6C-D), or in the anterior chamber of the eye (see, e.g., FIG. 6E). In embodiments wherein step 308 involves positioning the IOL in the anterior chamber of the eye, the IOL may be disposed such that corrugations of the IOL contact the anterior surface of the iris. The IOL may also be positioned in the anterior chamber of the eye such that peripheral portions (e.g., tabs 38*a-d*, FIG. 2A) of the IOL are disposed in the iridocorneal angle.

Figure 7C:
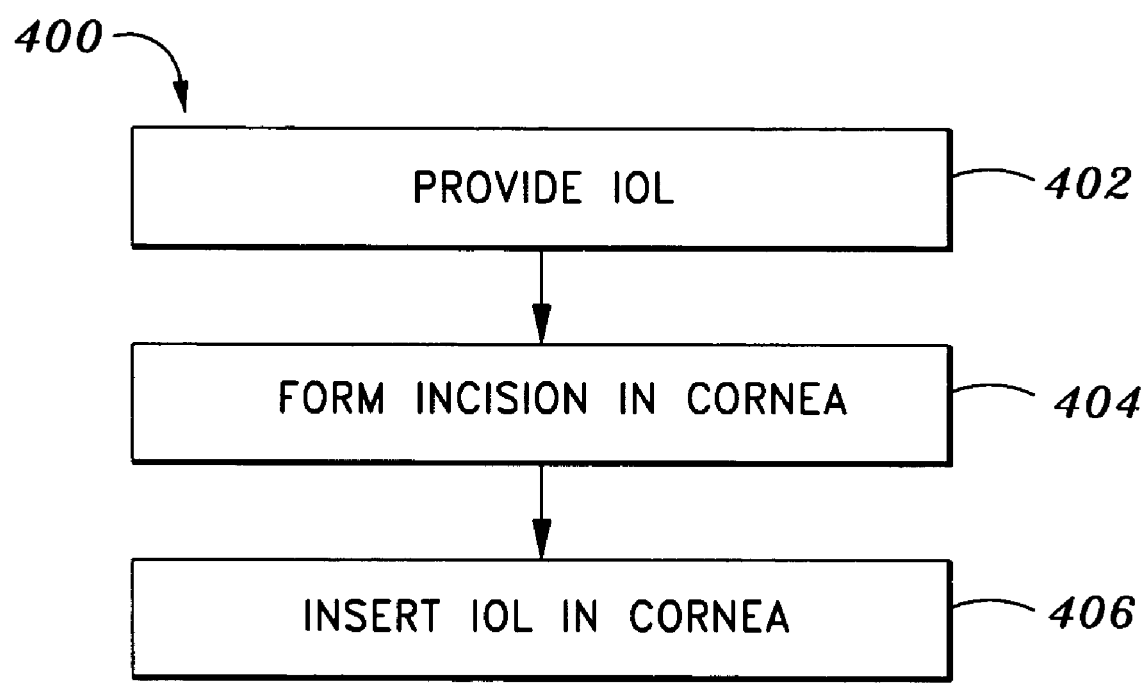
FIG. 7C schematically represents a series of steps involved in a method for inserting an IOL in the cornea of a patient, according to another embodiment of the invention.

FIG. 7C schematically represents a series of steps involved in a method 400 for inserting an IOL in the cornea of a patient, according to another embodiment of the invention, wherein step 402 may involve providing an IOL. The acronym IOL may be used here and in FIG. 7C in a generic sense to include an intracorneal lens of the present invention. The IOL, e.g., an intracorneal lens provided in step 402, may have features generally as described hereinabove, for example, with reference to step 202 (FIG. 7A). As an example, the IOL provided in step 402 may include an optical portion having a peripheral optic zone having optical power, and an inner non-optic zone having no optical power. In some embodiments, the IOL provided in step 402 may lack a haptic portion, e.g., the IOL may consist essentially of an optical portion. The IOL may be inserted in the cornea for correcting vision of the patient. The IOL provided in step 402 may be adapted to be deformable in order to facilitate insertion of the IOL in the cornea.

Step 404 may involve forming an incision in the cornea of the eye. Step 404 may involve forming a corneal flap or a corneal pocket. The formation of corneal flaps and corneal pockets are known in the art of eye surgery. As an example, a corneal flap may be formed using a laser. The laser may be used and guided under computer control, as is well known in the art. A corneal flap may be formed by methods similar to those used during LASIK (laser-assisted in-situ keratomileusis) procedures. A corneal pocket may be formed by tunneling in the cornea, for example, using a microkeratome having an oscillating metal blade. A corneal-pocket keratome device was disclosed in U.S. Pat. No. 6,599,305, the disclosure of which is incorporated by reference herein in its entirety. In alternative embodiments, a corneal pocket may be formed by a laser. Alternatively, a corneal pocket may be formed manually by the surgeon using hand-held instruments.

Step 406 may involve inserting the IOL in the cornea (see, for example, FIG. 6D). In alternative embodiments, step 406 may involve inserting the IOL beneath a corneal flap, or within a corneal pocket.

It should be understood, of course, that the foregoing relates to exemplary embodiments of the invention and that modifications may be made without departing from the spirit and scope of the invention as set forth in the following claims.

We claim:

1. An intraocular lens, comprising:

an optical portion, a haptic portion surrounding said optical portion, wherein said haptic portion is corrugated, and at least one irrigation channel disposed within said haptic portion.

2. The intraocular lens of claim 1, wherein said at least one irrigation channel is elongate and radially disposed with respect to said optical portion.

3. The intraocular lens of claim 1, wherein said at least one irrigation channel comprises at least two diametrically opposed irrigation channels.

4. The intraocular lens of claim 1, wherein said at least one irrigation channel is disposed entirely within said haptic portion.

5. The intraocular lens of claim 1, wherein said at least one irrigation channel is adapted for passage of aqueous humor therethrough.

6. An intraocular lens comprising:

an optical portion, a haptic portion surrounding said optical portion, wherein said haptic portion is corrugated, and a pair of orientation labels disposed within said haptic portion.

7. The intraocular lens of claim 6, wherein said pair of orientation labels are diametrically opposed.

8. The intraocular lens of claim 6, wherein each of said pair of orientation labels is disposed within a tab, said tab disposed peripherally on said haptic portion.

9. An intraocular lens comprising:

a central optical portion, and an outer haptic portion, wherein said haptic portion includes:

an annular portion disposed adjacent to, and radially outward from, said optical portion, a pair of inner arcuate corrugation disposed adjacent to, and radially outward from, said annular portion, said pair of inner arcuate corrugations disposed on opposite sides of said optical portion, a pair of outer arcuate corrugations disposed adjacent to, and radially outward from, said pair of inner arcuate corrugations, and at least one irrigation channel disposed within said haptic portion.

10. The intraocular lens of claim 9, further comprising a plurality of tabs, each of said tabs disposed peripherally on said haptic portion wherein:

said optical portion is axially spaced from said plurality of tabs, each of said optical portion and said haptic portion is deformable, and said at least one irrigation channel is elongate and radially disposed with respect to said optical portion.

11. An intraocular lens, comprising:

a central optical portion, and an outer haptic portion, wherein said haptic portion includes:

an annular portion disposed adjacent to, and radially outward from, said optical portion, a pair of inner arcuate corrugation disposed adjacent to, and radially outward from, said annular portion, said pair of inner arcuate corrugations disposed on opposite sides of said optical portion, a pair of outer arcuate corrugations disposed adjacent to, and radially outward from, said pair of inner arcuate corrugations, a plurality of tabs, each of said tabs disposed peripherally on said haptic portion, and wherein said haptic portion further includes a pair of diametrically opposed orientation labels, wherein said pair of orientation labels are disposed within a corresponding diametrically opposed pair of said tabs.

12. An intraocular lens, comprising:

an optical portion including a peripheral optic zone, and an inner non-optic zone surrounded by said peripheral optic zone, wherein:

said peripheral optic zone has optical power, and said inner non-optic zone has no optical power.

13. The intraocular lens of claim 12, wherein said intraocular lens consists essentially of said optical portion.

14. The intraocular lens of claim 13, wherein said lens is adapted for insertion within a cornea of a patient for vision correction of the patient.

15. The intraocular lens of claim 12, wherein said optical portion has a doughnut-like configuration.

16. The intraocular lens of claim 12, further comprising a haptic portion surrounding said optical portion.

17. The intraocular lens of claim 16, wherein said haptic portion is corrugated.

18. The intraocular lens of claim 12, wherein said optical portion is deformable.

19. A haptic for an intraocular lens, the intraocular lens including an optical portion, and said haptic comprising:

an annular portion encircling said optical portion, at least one arcuate corrugation disposed adjacent to, and radially outward from, said optical portion, and at least one irrigation channel radially disposed within said haptic.

20. A method for correcting vision of a patient, comprising:

a) providing a refractive lens, wherein said lens comprises an optical portion including a peripheral optic zone having optical power, and an inner non-optic zone surrounded by said peripheral optic zone, wherein said inner non-optic zone has no optical power;

b) forming an incision in a cornea of the patient; and c) inserting said lens in the cornea.

21. The method of claim 20, wherein said step b) comprises forming a corneal flap, and said step c) comprises inserting said lens beneath said corneal flap.

22. The method of claim 21, wherein said step b) comprises forming said corneal flap using a laser.

23. The method of claim 20, wherein said step b) comprises forming a corneal pocket, and said step c) comprises inserting said lens beneath said corneal pocket.

24. The method of claim 23, wherein said corneal pocket is formed by a laser or by a microkeratome.

25. An intraocular lens, comprising:

an optical portion, an irrigation channel disposed within said optical portion, and a haptic portion surrounding said optical portion, wherein said haptic portion is corrugated.

26. The intraocular lens of claim 25, wherein said irrigation channel comprises a hole.

27. The intraocular lens of claim 26, where in said hole is circular in configuration.

28. An intraocular lens comprising:

a central optical portion, an irrigation channel disposed within said optical portion, and an outer haptic portion, wherein said haptic portion includes:

an annular portion disposed adjacent to, and radially outward from, said optical portion, a pair of inner arcuate corrugation disposed adjacent to, and radially outward from, said annular portion, said pair of inner arcuate corrugations disposed on opposite sides of said optical portion, and a pair of outer arcuate corrugations disposed adjacent to, and radially outward from, said pair of inner arcuate corrugations.

29. The intraocular lens of claim 28, wherein said irrigation channel comprises a circular hole.

30. A haptic for an intraocular lens, the intraocular lens including an optical portion, and said haptic comprising:

an annular portion encircling said optical portion, at least one arcuate corrugation disposed adjacent to, and radially outward from, said optical portion, and an irrigation channel disposed within said optical portion.

31. The haptic of claim 30, wherein said irrigation channel comprises a circular hole substantially in a center of said optical portion.

32. A method for correcting vision of a patient, comprising:

a) providing a refractive intraocular lens, wherein said intraocular lens comprises an optical portion and a haptic portion, wherein said lens further comprises a hole in said optical portion, and wherein said haptic portion is corrugated;

b) forming an incision in an eye of the patient; and c) inserting said intraocular lens in the eye.

* * * * *